United States Patent [19]

Shephard

[11] Patent Number: 4,529,798
[45] Date of Patent: Jul. 16, 1985

[54] PROCESS FOR PREPARING CYANO DERIVATIVES OF TETRAHYDROQUINOLINES AND RELATED COMPOUNDS

[75] Inventor: Robin G. Shephard, Burnham, England

[73] Assignee: John Wyeth & Brother Limited, Maidenhead, England

[21] Appl. No.: 326,468

[22] Filed: Dec. 2, 1981

[30] Foreign Application Priority Data

Dec. 9, 1980 [GB] United Kingdom ............... 8039423

[51] Int. Cl.³ .................. C07D 215/18; C07D 219/04; C07D 221/12; C07D 221/16
[52] U.S. Cl. ..................................... 546/93; 546/104; 546/108; 546/109; 546/111; 546/173; 546/176; 546/177
[58] Field of Search ................ 546/177, 93, 104, 108, 546/109, 111, 173, 176

[56] References Cited

U.S. PATENT DOCUMENTS 3,991,060 11/1976 Curran ................................. 546/177
4,160,094 7/1979 Curran et al. ........................ 546/152

FOREIGN PATENT DOCUMENTS 1432378 4/1976 United Kingdom ............... 546/177

OTHER PUBLICATIONS

Lettré et al., Chem. Ber., 85, 1952, pp. 397–407.

Primary Examiner—Donald G. Daus
Assistant Examiner—William A. Teoli, Jr.
Attorney, Agent, or Firm—George Tarnowski

[57] ABSTRACT

Fused carbocyclic ring derivatives of pyridine which contain a nitrile or thioamide group on the carbocyclic ring e.g. 8-cyano or thiocarboxamido-5,6,7,8-tetrahydroquinolines are prepared by a process in which a sodium, potassium, lithium or magnesium halide derivative of the pyridine compound is treated with a compound RaRbNCN wherein Ra and Rb are the same or different and represent alkyl, cycloalkyl, or aralkyl, or Ra and Rb are joined to form a heterocyclic ring with the nitrogen, and the product is treated with a proton source to obtain the nitrile which is optionally treated with a sulphurizing agent to form the thioamide. The nitriles or thioamides may be isolated as their acid addition salts.

7 Claims, No Drawings

PROCESS FOR PREPARING CYANO DERIVATIVES OF TETRAHYDROQUINOLINES AND RELATED COMPOUNDS

The invention relates to a process for preparing pyridine derivatives which have value as anti-ulcer/anti-secretory agents.

UK Patent Specification No. 1,432,378 describes fused carbocyclic ring derivatives of pyridine, for example 8-cyano-5,6,7,8-tetrahydroquinolines and the corresponding thioamides which are either anti-ulcer/anti-secretory agents or intermediates for such agents.

Analogous nitriles and thioamides are described in UK Patent Specifications Nos. 1,495,993 and 1,458,148. Further examples of such nitriles and thioamides are given in UK Specifications Nos. 1,463,668; 1,463,669 and 1,471,371.

These specifications describe various ways of making the nitriles and thioamides. However, it has been found that the previously described methods do not always give high yields of the desired end product. We have now found a new method for preparing the nitriles and thioamides which is often superior to the previous routes.

According to the present invention there is provided a process for preparing compounds of Formula I

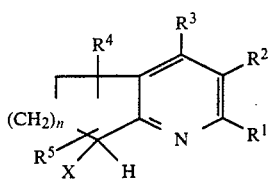

or acid addition salts thereof, wherein $R^1$, $R^2$, $R^3$, $R^4$ and $R^5$ are the same or different and represent hydrogen, alkyl, cycloalkyl, aralkyl, or aryl radicals, any of which radicals may be substituted or $R^1$ and $R^2$ taken together, or $R^2$ and $R^3$ taken together, form a 5,6, or 7 membered ring which may be saturated or unsaturated and substituted or unsubstituted, $R^4$ and $R^5$ may also represent alkoxy, n is 1,2 or 3 and X is CN or CSNHR characterised in that a compound of Formula II

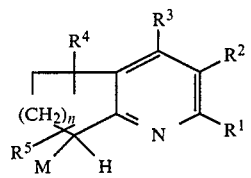

wherein $R^1$, $R^2$, $R^3$, $R^4$, $R^5$ and n are as defined above, and M is lithium, sodium, potassium, or MgHal, where Hal is chlorine, bromine or iodine, is reacted with a compound of Formula RaRbNCN wherein Ra and Rb are the same or different and represent alkyl, cycloalkyl or aralkyl, or Ra and Rb may be joined to form a heterocyclic ring with the nitrogen atom to which they are attached and the product is treated with a proton source to obtain a nitrile of Formula I wherein X is CN and if desired the nitrile is treated with a sulphurising agent to obtain a thioamide of Formula I wherein X is CSNHR where R is hydrogen or lower alkyl and optionally the compound of Formula I is isolated as an acid addition salt. The starting compounds of Formula II may be prepared as discussed in any of the aforementioned prior UK Patent Specifications, or in UK Patent Specifications Nos. 1,463,665 and 1,463,666. The preferred method for introducing the metal ion M is as described in UK Patent 1,463,666 namely by reaction of a corresponding compound of Formula II wherein M is hydrogen with a metal alkyl $MR^6$ wherein M is sodium, potassium or lithium and $R^6$ is alkyl, (e.g. n-butyl), aralkyl or aryl e.g. phenyl or mesityl (2,4,6-trimethylphenyl) or with a metal amide MA wherein M is sodium, potassium or lithium and A is an amine radical, preferably a secondary amine.

The metal amide may be formed in situ by reacting a metal compound $MR^6$ as defined above with an amine $R^9R^{10}NH$, wherein $R^9$ and $R^{10}$ have the same meanings as Ra and Rb, or $R^9$ is hydrogen, preferably in a molar amount equal to that of the metal alkyl. The amine is preferably a secondary amine such as a dialkylamine, e.g. diethylamine, di-isopropylamine, di-t-butylamine, di-n-decylamine, dicyclohexylamine, N-t-amyl-N-t-butylamine, N-isopropyl-N-cyclohexylamine, N-t-butyl-N-cyclohexylamine, N-t-butyl-α-methylbenzylamine or N(1-ethylcyclohexyl)-1,1,3,3,-tetramethylbutylamine or a cyclic amine e.g. piperidine, or an alkyl substituted piperidine e.g. 2,2,6,6-tetramethylpiperidine. Preferred amines are hindered amines such as one in which $R^9$ and $R^{10}$ are selected from secondary or tertiary radicals or cycloalkyl radicals, especially when $R^3$ is alkyl.

When forming the starting compound of Formula II from a corresponding compound in which M is hydrogen the yield may be reduced by competing reactions when $R^1$ or $R^3$ contain exchangeable hydrogen atoms, e.g. when $R^1$ or $R^3$ are alkyl. In such cases a mixture may be formed with the desired compound of Formula II and one in which M is hydrogen and there is a metal substituent on $R^1$ or $R^3$. The reaction with RaRbNCN then produces as impurity a compound with the CN group in the radical $R^1$ or $R^3$. The mixture of desired product of Formula I and impurity may be separated by conventional methods, e.g. crystallisation, chromatography, distillation and so on. When competing metallations are liable to occur, it is possible to favour formation of compound II by appropriate choice of reaction conditions and/or reagents. For example when $R^3$ is alkyl it has been found that formation of the compound of Formula II is favoured or exclusive when the starting compound wherein M is hydrogen is added to a solution of a small excess of the metal alkyl or up to 2.5 molar equivalents of the metalamide, rather than the converse.

When an alkyl group $R^3$ is present in compound II it has been found that the reaction with compound RaRbNCN may still produce some of the "wrong" isomer. The amount of "wrong" isomer can be considerably reduced by adding compound II to a refluxing solution of RaRbNCN instead of the reverse of this procedure. Yields are even higher when metal amide (preferably a molar equivalent of metal amide) is present during the reaction with compound RaRbNCN. If the starting compound II is formed in situ using 2 molar equivalents of metal amide this provides the excess metal amide for use during the reaction with RaRbNCN. It has also been found that when the metal amide is of a hindered secondary amine, e.g. N-t-butyl-N-cyclohexylamine, formation of the desired isomer is favoured.

The process of the invention is carried out by reacting compound II with RaRbNCN in a suitable solvent e.g. a hydrocarbon solvent such as benzene, toluene or xylene or an ether solvent e.g. ether, tetrahydrofuran or dioxan. The temperature may range from −70° C. to the reflux temperature of the solvent e.g. −20° C. to 80° C. A mixture of solvents may be used e.g. the compound II may be prepared in situ in a different solvent from that in which the reaction with RaRbNCN takes place e.g. hexane.

The compound RaRbNCN may be added to a refluxing solution of compound II or vice versa but it is preferred to add compound II to refluxing RaRbNCN when R³ is lower alkyl in compound II. It is also preferable to keep the reaction time short e.g. up to 3 hours.

When any of R¹, R², R³, R⁴, R⁵, R⁶, Ra, Rb or R is an alkyl radical, a lower alkyl of 1–6 carbon atoms is preferred. This may be straight or branched chain e.g. methyl, ethyl, n- and iso propyl, n, s- and t-butyl, pentyl or hexyl. When any of R¹,R²,R³,R⁴,R⁵, Ra or Rb is a cycloalkyl radical this preferably has from 4 to 6 carbon atoms.

When any of R¹,R²,R³,R⁴,R⁵,R⁶, Ra or Rb is an aralkyl radical this is preferably aryl lower alkyl in which the lower alkyl portion has 1–6 carbon atoms and may be any of the radicals specified above for a lower alkyl radical.

An aryl radical as used herein is preferably phenyl, which may be substituted e.g. by alkyl, alkoxy, fluorine, or trifluoromethyl. The alkyl and alkoxy radicals are preferably lower alkyl as discussed above or lower alkoxy in which the alkyl portion is as described above for a lower alkyl radical.

Aralkyl radicals may be substituted on the aryl portion as discussed above for an aryl radical.

Any of the alkyl radicals mentioned above may be substituted by alkoxy or trifluoromethyl.

The reagent RaRbNCN is preferably diisopropyl cyanamide but other examples are dimethyl cyanamide, diethyl cyanamide, ditert-butyl cyanamide, dicyclohexyl cyanamide, N-t-butyl-N-cyclohexyl cyanamide, 1-cyano-piperidine or 1-cyano 2,2,6,6-tetramethylpiperidine. Preferably Ra and Rb are chosen from secondary and tertiary alkyl radicals or cycloalkyl radicals. The product of reaction of RaRbNCN and Compound II is treated with a proton source such as water, e.g. in the form of an aqueous acid or other aqueous medium, an alkanol, e.g. of 1–6 carbon atoms, or ammonium chloride which can be added as a solid or in solution.

The nitriles of Formula I may be used either as anti-ulcer/anti-secretory agents or converted to the corresponding thioamides by treatment with a sulphurising agent e.g. by treatment with H₂S(optionally in the presence of a lower alkylamine RNH₂) or a thioamide R⁷CSNH₂ wherein R⁷ is an alkyl group in a solvent such as pyridine, a lower alkanol, dioxane, dimethyl formamide, dimethyl sulphoxide, sulpholane. A base such as a trialkylamine may be present. Alternatively the sulphurising agent may be a dithio compound of formula (R⁸)₂ PSSH wherein R⁸ is alkyl, aralkyl, aryl, alkoxy, aralkoxy or aryloxy which is used in the presence of a hydrogen halide. A thioamide of Formula I wherein X is CSNH₂ may be converted into a thioamide where X is CSNHR by treatment with a lower alkylamine. The reaction may be carried out with or without an inert solvent, suitable solvents for the reaction with the dithio acid include chlorinated hydrocarbons such as dichloromethane, dichloroethane, chloroform, carbon tetrachloride or hydrocarbons such as benzene and toluene. Particularly preferred dithio acids are diethyldithiophosphate and diphenylphosphinodithioic acid.

The nitriles or thioamides may be converted to acid addition salts with inorganic acids e.g. hydrochloric, hydrobromic, sulphuric or nitric acids or organic acids e.g. citric, fumaric, maleic, or tartaric acids or organic sulphonic acids such as alkyl sulphonic acids e.g. methane sulphonic acid or aryl sulphonic acids e.g. p-toluene sulphonic acid.

Preferably the compounds prepared according to the invention have Formula III

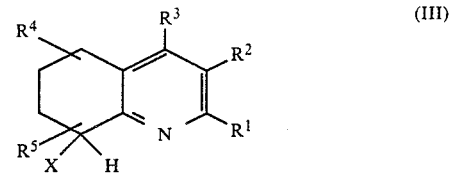

wherein R¹,R²,R³,R⁴,R⁵ and X are as defined above.

Especially preferred are those compounds obtained from a starting material of Formula IV

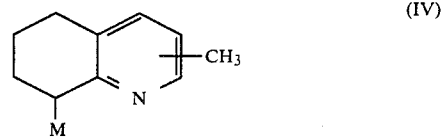

wherein M is as defined above.

EXAMPLE 1

8-Cyano-4-methyl-5,6,7,8-tetrahydroquinoline

A solution of 4-methyl-5,6,7,8-tetrahydroquinoline (73.5 g, 0.5M) in tetrahydrofuran (300 ml) was added to a 1.6M solution of butyl lithium in hexane (344 ml, 0.55M) maintained at 0° C. After 10 min. the resulting red anion solution was added to a refluxing mixture of diisopropyl cyanamide (94.5 g, 0.75M) in tetrahydrofuran (300 ml). The reaction mixture was cooled and poured on to iced water (500 ml) neutralised with 12M hydrochloric acid and the organic solvent removed under reduced pressure. The residue was adjusted to pH 1 (12M HCl) and extracted with ethyl acetate (2×500 ml). The aqueous phase was adjusted to pH 10 (potassium carbonate) and extracted with dichloromethane (3×300 ml). The final organic extracts were dried and the solvent removed. The residue was dissolved in methanol and treated with an excess of ethereal hydrogen chloride. Removal of the resulting crystals by filtration gave the title compound as the hydrochloride (73 g, 70%) identical with authentic material. mp 253°–5° C. Found: C,63.0, H,6.7; N,13.1, C₁₁H₁₂N₂.HCl requires C,63.3; H,6.3; N,13.4%.

EXAMPLE 2

8-Cyano-5,6,7,8-tetrahydroquinoline

A solution of 5,6,7,8-tetrahydroquinoline (6.5 ml, 50 mM) in benzene (35 ml) maintained below 10° was treated with 1.6M butyl lithium in hexane (31.25 ml, 50 mM). The resulting anion solution was heated to reflux then treated with a solution of diisopropylcyanamide (6.3 g, 50 mM) in benzene (15 ml). After 15 min. the mixture was cooled and quenched with water (20 ml). The organic phase was separated, dried and evaporated.

Distillation of the residue gave the title compound (5.6 g, 71%) Bp. 135°-140°/2 mm, identical with authentic material. Hydrochloride mp 185° C.—see Example 37 UK Pat. No. 1,432,378.

EXAMPLE 3

8-Cyano-5,6,7,8-tetrahydroquinoline

A solution of 8-lithio-5,6,7,8-tetrahydroquinoline (10 mM) was generated from 5,6,7,8-tetrahydroquinoline (1.3 ml), ether (6 ml) and 1.6M butyl lithium in hexane (6.25 ml), then added to a solution of diisopropylcyanamide (3.9 g, 30 mM) in ether (6 ml) at 0° C.

Work up of the reaction mixture after 15 minutes as described in Example 2 gave the title compound in 85% yield.

EXAMPLE 4

8-Cyano-3-methyl-5,6,7,8-tetrahydroquinoline

Following the procedure of Example 1 3-methyl-5,6,7,8-tetrahydroquinoline is treated with butyllithium in hexane and then the reaction mixture is added to a refluxing solution of diisopropyl cyanamide in tetrahydrofuran. The reaction mixture is treated with water and the title compound isolated as the hydrochloride, after the manner of Example 1, mp 189° C.

EXAMPLE 5

Following the procedure of Example 1 but using alternative starting materials, the following compounds are prepared

| | Starting Material | RaRbNCN | Product |
|---|---|---|---|
| a | 2-Phenyl-5,6,7,8-tetrahydroquinoline | diisopropyl-cyanamide | 8-cyano-2-phenyl-5,6,7,8-tetrahydroquinoline |
| b | 2-t-Butyl-5,6,7,8-tetrahydroquinoline | diisopropyl-cyanamide | 2-t-butyl-8-cyano-5,6,7,8-tetrahydroquinoline |
| c | 2-Methyl-5,6,7,8-tetrahydroquinoline | dicyclohexyl cyanamide | 8-cyano-2-methyl-5,6,7,8-tetrahydroquinoline |
| d | sym-Octahydroacridine | di-t-butyl-cyanamide | 4-cyano-sym-octahydroacridine |
| e | 3,4-Dimethyl-5,6,7,8-tetrahydroquinoline | diisopropyl cyanamide | 8-cyano-3,4-dimethyl-5,6,7,8-tetrahydroquinoline |
| f | 3,5-Dimethyl-5,6,7,8-tetrahydroquinoline | 1-cyano-piperidine | 8-cyano-3,5-dimethyl-5,6,7,8-tetrahydroquinoline |
| g | 3,6-Dimethyl-5,6,7,8-tetrahydroquinoline | diethyl cyanamide | 8-cyano-3,6-dimethyl-5,6,7,8-tetrahydroquinoline |
| h | 1,2,3,4,7,8,9,10-Octahydrophenanthridine | diisopropyl cyanamide | 4-cyano-1,2,3,4,7,8,9,10-Octahydrophenanthridine |
| i | 2,3,5,6,7,8-Hexahydro-1-H—cyclopenta[b]quinoline | dimethyl cyanamide | 5-cyano-2,3,5,6,7,8-hexahydro-1-H—cyclopenta[b]quinoline |
| j | 3-Methyl-cyclopenteno[b]pyridine | N—t-butyl, N—cyclohexyl cyanamide | 7-cyano-3-methyl-cyclopenteno[b]pyridine |

EXAMPLE 6

3-methyl-5,6,7,8-tetrahydroquinoline-8-thiocarboxamide (A) 8-Cyano-3-methyl-5,6,7,8-tetrahydroquinoline (8.8 g, 50 mM) in dichloromethane (50 ml) and diethyl dithiophosphate (8.4 ml, 50 mM) were treated with HCl gas at reflux. After 2.5 hours reaction mixture was cooled to ambient temp and ether (250 ml) added. The resulting precipitate was removed by filtration, washed with ether and recrystallised from ethanol to give the title compound as the hydrochloride (11.1 g, 90%). mp 219° C. identical with an authentic sample—see Example 18 of U.K. Pat. No. 1,432,378.

(B) The above reaction was repeated using dichloroethane as solvent instead of dichloromethane. The reaction was complete in 1 hour giving the title compound as the hydrochloride in 95% yield.

EXAMPLE 7

4-methyl-5,6,7,8-tetrahydroquinoline-8-thiocarboxamide

A mixture of 8-cyano-4-methyl-5,6,7,8-tetrahydroquinoline (73 g, 0.35M), diethyl dithiophosphate (60 ml, 0.36M) and dichloroethane (350 ml) was treated with HCl gas at reflux over 4 hours. The mixture was then cooled to ambient temperature, filtered and the product washed with dichloroethane, then recrystallised from methanol—ether to give the title compound as the hydrochloride (74.5 g, 88%) mp 213° C. identical with an authentic sample—see Example 1 of UK Pat. No. 1,463,669.

EXAMPLE 8

Following the procedure of Example 6A the nitriles listed in Example 5 are converted to the corresponding thioamides:

(a) 2-Phenyl-5,6,7,8-tetrahydroquinoline-8-thiocarboxamide.

(b) 2-t-butyl-5,6,7,8-tetrahydroquinoline-8-thiocarboxamide.

(c) 2-methyl-5,6,7,8-tetrahydroquinoline-8-thiocarboxamide.

(d) sym-octahydroacridine-4-thiocarboxamide.

(e) 3,4-dimethyl-5,6,7,8-tetrahydroquinoline-8-thiocarboxamide.

(f) 3,5-dimethyl-5,6,7,8-tetrahydroquinoline-8-thiocarboxamide.

(g) 3,6-dimethyl-5,6,7,8-tetrahydroquinoline-8-thiocarboxamide.

(h) 1,2,3,4,7,8,9,10-octahydrophenanthridine-4-thiocarboxamide.

(i) 2,3,5,6,7,8-hexahydro-1-H-cyclopenta[b]quinoline-5-thiocarboxamide.

(j) 3-methyl-cyclopenteno[b]pyridine-7-thiocarboxamide

EXAMPLE 9

5,6,7,8-Tetrahydroquinoline-8-thiocarboxamide

A mixture of 8-cyano-5,6,7,8-tetrahydroquinoline (5.4 g, 34 mM) dichloromethane (100 ml) and diethyl dithiophosphate (5.75 ml) was maintained at reflux and treated with hydrogen chloride gas. After 8 hours the mixture was cooled to ambient temperature and diluted with ether. The resulting precipitate was washed well with ether and recrystallised from methanol/ether to give the title compound as the hydrochloride (7.0 g 90%) mp 263° C.

EXAMPLE 10

8-Cyano-4-methyl-5,6,7,8-tetrahydroquinoline

A solution of 1.55M butyl lithium in hexane (35.5 ml, 55 mM) maintained at 0° to 5° C. under argon was treated successively with N-t-butylcyclohexylamine (4.65 g, 30 mM) and a solution of 4-methyl-5,6,7,8-tetrahydroquinoline (3.67 g, 25 mM) in tetrahydrofuran (10 ml). After 0.5 hours at about 5° C. a solution of di-isopropylcyanamide (3.5 g, 28 mM) was added in tetrahydrofuran (10 ml) and the mixture stirred a further 0.5 hours at 0° C. The mixture was quenched with water (50 ml), the aqueous layer extracted with toluene (50 ml), the combined organic phases dried and evaporated. Removal of t-butylcyclohexylamine under reduced pressure left an oil which contained (nmr analysis) 89% of the title compound and 11% 4-cyanomethyl-5,6,7,8-tetrahydroquinoline. Pure title compound was isolated by conversion to the hydrochloride in methanol as in Example 1.

EXAMPLE 11

7-Cyanocyclopenteno[b]-pyridine

A solution of lithium diisopropylamide [made ex 1.55M BuLi/hexane (64.5 ml, 0.1M), diisopropylamine (14 ml, 0.1M) tetrahydrofuran (30 ml)] maintained at 0° C. under argon was treated with a solution of cyclopenteno[b] pyridine (5.96 g, 50 mM) in tetrahydrofuran (10 ml). After 0.5 hours a solution of diisopropylcyanamide (7.0 g, 55 mM) in tetrahydrofuran (10 ml) was added. After a further 0.5 hours the reaction mixture was quenched with water, extracted with toluene, the organic phase washed with water, dried and evaporated. The residue was dissolved in ether/isopropanol and treated with an excess of ethereal hydrogen chloride. Removal of the resulting precipitate by filtration gave the title compound as the hydrochloride (5.6 g)mp 170° C.(sublimes)

EXAMPLE 12

4-Cyano-1,2,3,4,5,6,7,8-octahydroacridine

A solution of lithium diisopropylamide [ex 1.55M BuLi/hexane (32.3 ml, 50 mM), diisopropylamine (3.5 ml, 25 mM), tetrahydrofuran (20 ml)] maintained at 0° C. under an argon atmosphere was treated with a solution of octahydroacridine (4.68 g, 25 mM) in the tetrahydrofuran (10 ml). After 0.5 hours a solution of N-t-butyl-N-cyclohexylcyanamide (4.6 g, 28 mM) in tetrahydrofuran (10 ml) was added and the mixture stirred overnight. The reaction was quenched with water, extracted with toluene and the organic phase washed with water, dried and evaporated. The residue, dissolved in ethyl acetate, was passed through a short silica column to yield the title compound. (3.8 g) mp. 88°–90° C.

I claim:

1. A process for preparing compounds of the formula

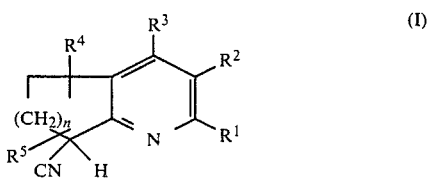

(I)

and acid addition salts thereof, wherein $R^1$, $R^2$, $R^3$, $R^4$ and $R^5$ are the same or different and represent hydrogen, lower alkyl, loweralkoxyloweralkyl, trifluoromethylloweralkyl, cycloalkyl of 4 to 6 carbon atoms, phenylloweralkyl of 7 to 12 carbon atoms and phenyl groups and a phenyl group or phenyl portion of a phenylloweralkyl group may be mono- or di-substituted by loweralkyl, lower alkoxy, fluorine or trifluoromethyl, or $R^1$ and $R^2$ taken together, or $R^2$ and $R^3$ taken together, form a 5, 6 or 7 membered saturated ring and $R^4$ and $R^5$ may also represent lower alkoxy, and n is 1, 2 or 3, wherein a compound of formula II

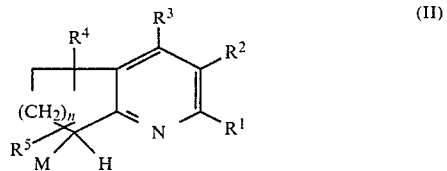

(II)

wherein $R^1$, $R^2$, $R^3$, $R^4$, $R^5$ and n are as defined above, and M is lithium, sodium, potassium or MgHal, where Hal is chlorine, bromine or iodine, is reacted with a compound of formula RaRbNCN wherein Ra and Rb are the same or different and represent loweralkyl, cycloalkyl of 4 to 6 carbon atoms or phenylalkyl of 7 to 12 carbon atoms, or Ra and Rb may be joined to form a 5- or 6-membered ring with the nitrogen and the product is treated with a proton source to obtain a nitrile of formula I, and if an acid addition salt is desired treating the nitrile of formula I with a pharmaceutically acceptable acid.

2. A process as claimed in claim 1, wherein the compound RaRbNCN is diisopropylcyanamide, or N-t-butyl-N-cyclohexyl cyanamide.

3. A process as claimed in claim 1, wherein the reaction of Compound II and RaRbNCN is carried out by adding Compound II to a solution of RaRbNCN.

4. A process as claimed in claim 1, wherein the reaction of Compound II with RaRbNCN is carried out in the presence of a metal amide.

5. A process as claimed in claim 4 characterised in that the metal amide has Formula MA wherein M is sodium, potassium or lithium and A is a secondary amine radical $-NR^9R^{10}$ wherein $R^9$ and $R^{10}$ have the same meanings as Ra and Rb.

6. A process as claimed in claim 5, characterised in that the compound RaRbNCN is diisopropylcyanamide and the secondary amine radical is N-t-butyl-N-cyclohexylamine.

7. A process for preparing compounds of formula Ia

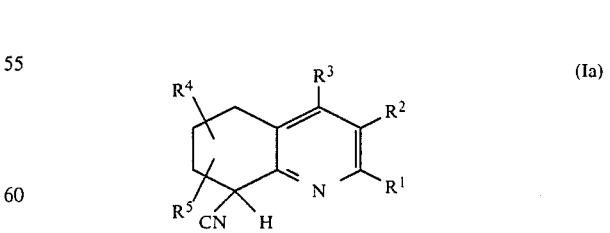

(Ia)

and acid addition salts thereof wherein $R^1$, $R^2$ and $R^3$ are the same or different and represent hydrogen or lower alkyl, $R^4$ and $R^5$ are the same or different and represent hydrogen, lower alkyl or lower alkoxy, in which a compound of formula IIa

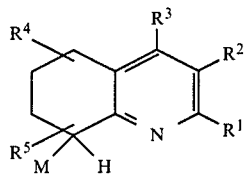
(IIa)

wherein $R^1$, $R^2$, $R^3$, $R^4$ and $R^5$ are as defined above and M is lithium, sodium or potassium is reacted with a compound of formula RaRbNCN wherein Ra and Rb are the same or different and represent loweralkyl, cycloalkyl of 4 to 6 atoms or phenylalkyl of 7 to 12 carbon atoms, or Ra and Rb may be joined to form a 5- or 6-membered ring with the nitrogen and the product is treated with a proton source to obtain a nitrile of formula Ia and if an acid addition salt is desired treating the obtained compound of formula Ia with a pharmaceutically acceptable acid.

* * * * *